United States Patent [19]

Takayama et al.

[11] Patent Number: 4,722,340
[45] Date of Patent: Feb. 2, 1988

[54] STONE DISINTEGRATOR APPARATUS

[75] Inventors: Syuichi Takayama; Kowji Tanikawa; Ryouji Masubuchi; Kunio Kinoshita; Minoru Shinozuka; Kenichirou Sanagi; Naoki Uchiyama, all of Tokyo; Yoshio Shishido, Sagamihara, all of Japan

[73] Assignee: Olympus Optical Co., Ltd., Tokyo, Japan

[21] Appl. No.: 36,172

[22] Filed: Apr. 8, 1987

Related U.S. Application Data

[63] Continuation of Ser. No. 803,342, Dec. 2, 1985, abandoned.

[30] Foreign Application Priority Data

Dec. 5, 1984 [JP] Japan ............................ 59-256819
Sep. 27, 1985 [JP] Japan ............................ 60-214323

[51] Int. Cl.⁴ .................................... A61B 17/22
[52] U.S. Cl. ............................................. 128/328
[58] Field of Search ............... 128/328, 303.14, 303.17

[56] References Cited

U.S. PATENT DOCUMENTS 4,1091,189  3/1980  Barkan ........................ 128/328
3,163,165  12/1964  Isikawa ..................... 128/303.17

FOREIGN PATENT DOCUMENTS 3316837  11/1984  Fed. Rep. of Germany .

Primary Examiner—Michael H. Thaler
Attorney, Agent, or Firm—Frishauf, Holtz, Goodman & Woodward

[57] ABSTRACT

A stone disintegrator apparatus has a probe with discharge electrodes and a power supply circuit for supplying a discharge voltage to the probe for causing discharge between the discharge electrodes. An electrode life detection circuit detects the number of use or discharge operations of the probe so as to determine the remaining life of the discharge electrodes. A discharge inhibit circuit inhibits re-use or discharge of the probe when the life detection circuit detects an end of electrode life.

27 Claims, 56 Drawing Figures

F I G. 11
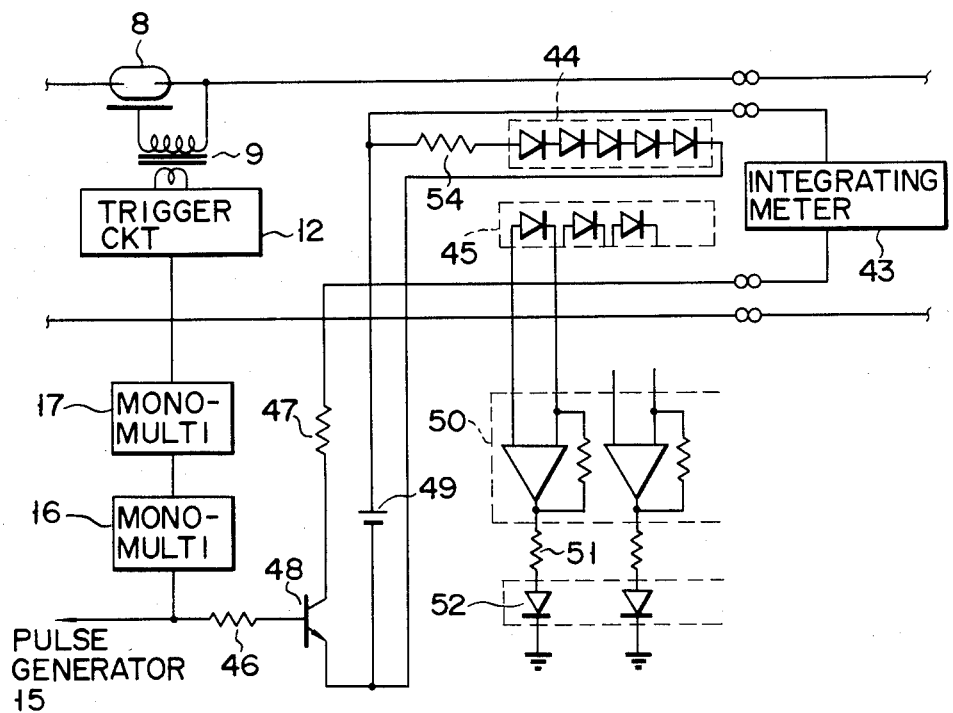
F I G. 12
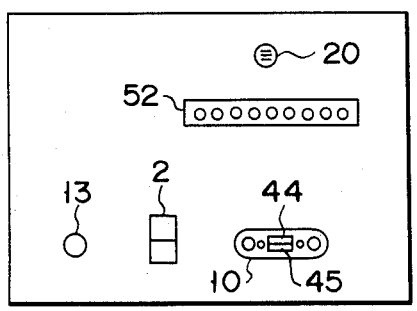
F I G. 13
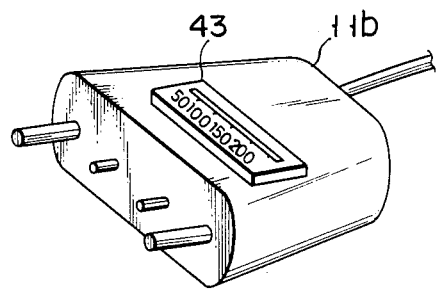

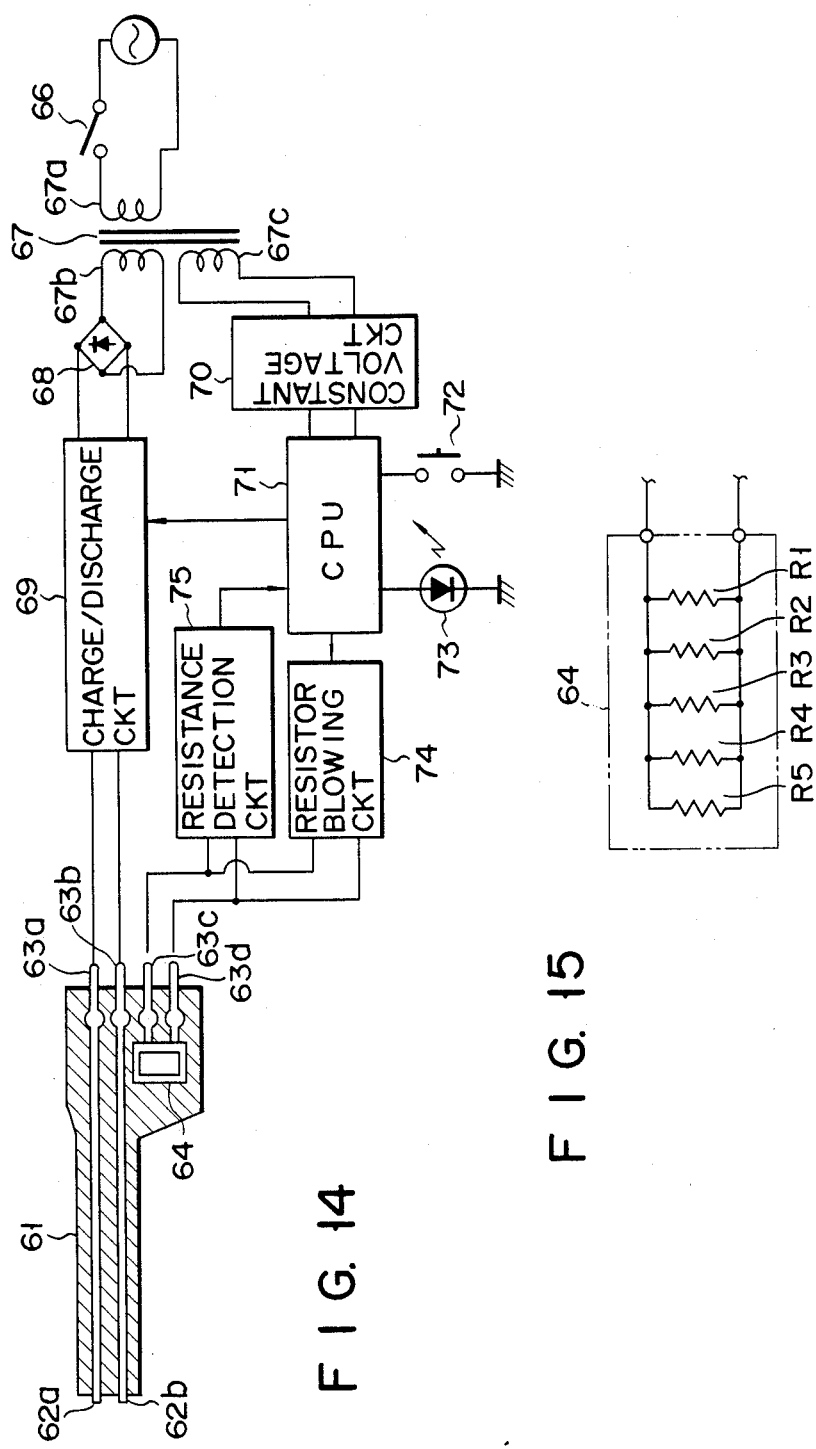
F I G. 14
F I G. 15

F I G. 22
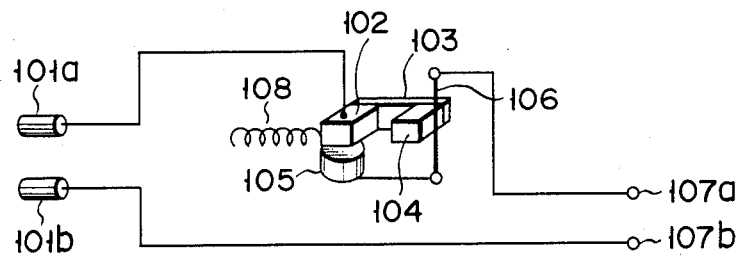
F I G. 23
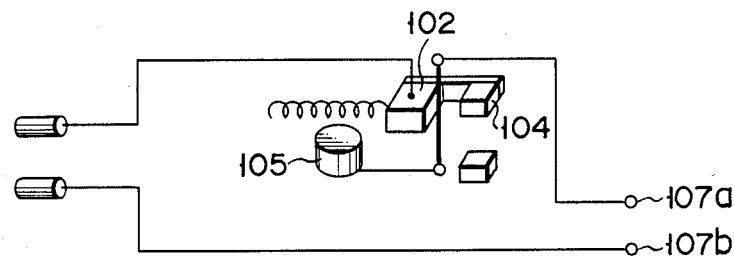
F I G. 24
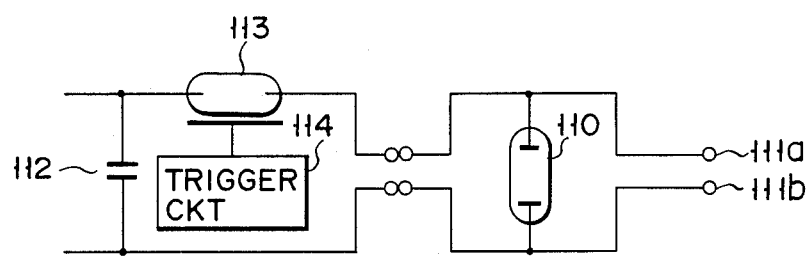

F I G. 25
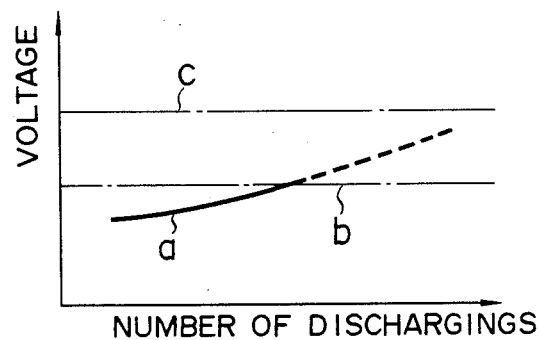
F I G. 26
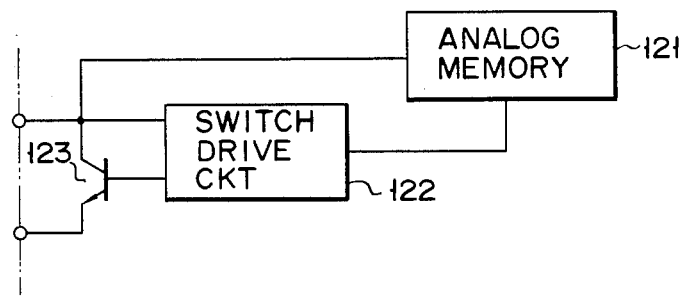
F I G. 27
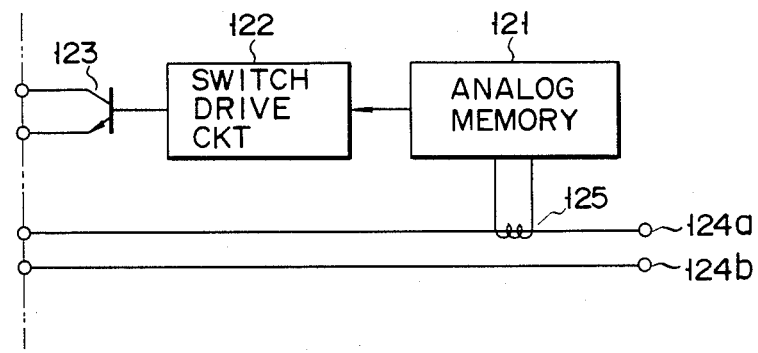

F I G. 45
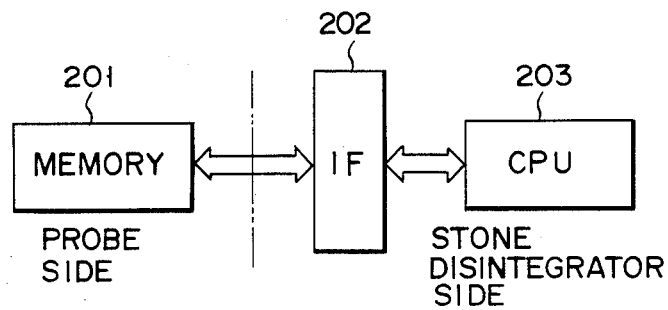
F I G. 46
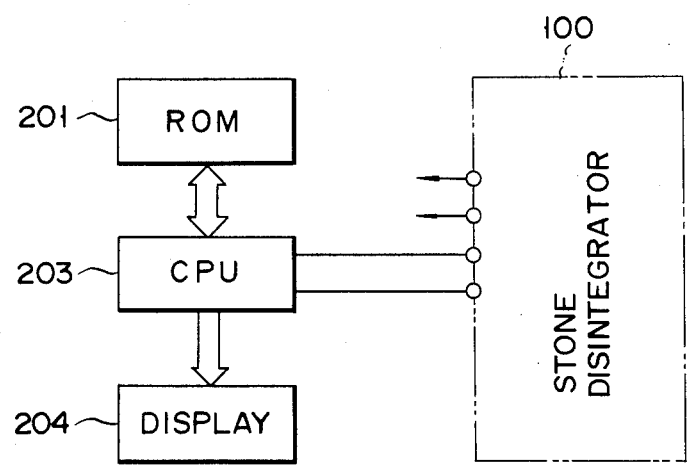

F I G. 47
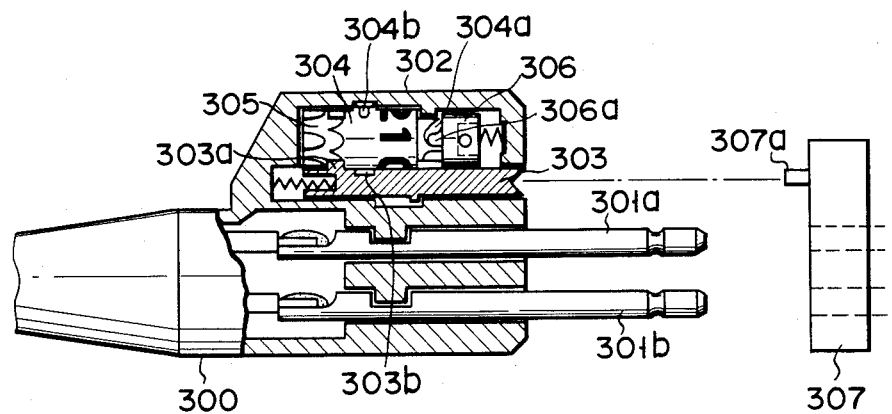
F I G. 48
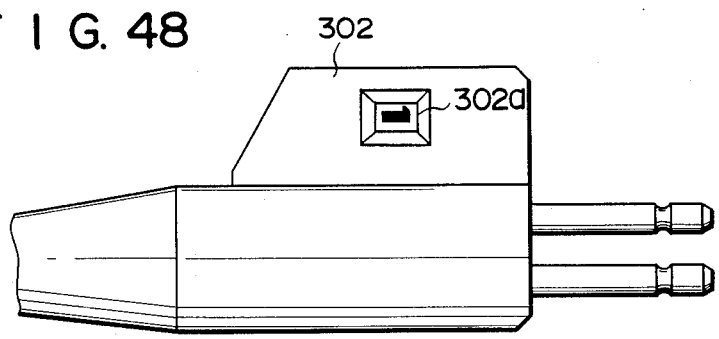
F I G. 49
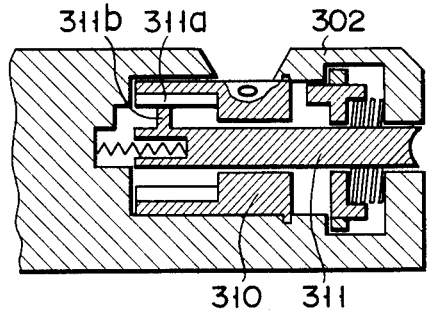

F I G. 50
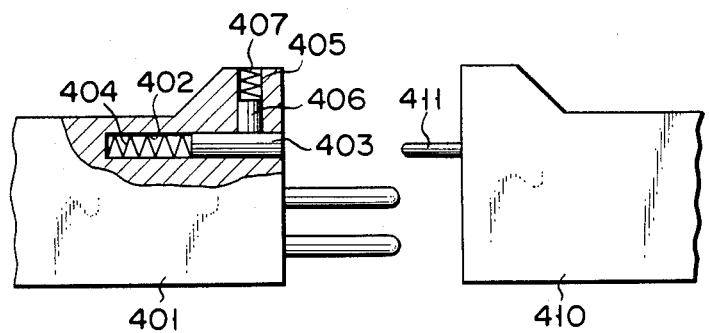
F I G. 51
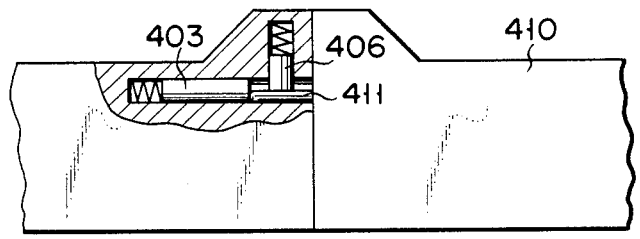
F I G. 52
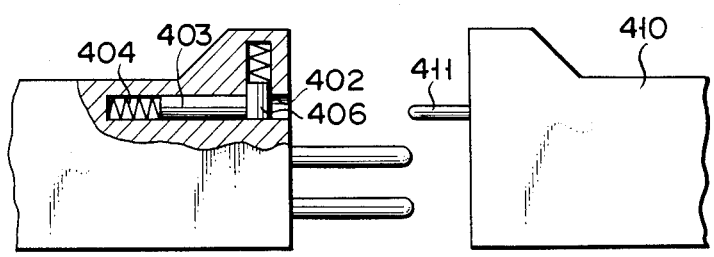

STONE DISINTEGRATOR APPARATUS

This application in a continuation of application Ser. No. 803,342, filed Dec. 2, 1985, now abandoned.

BACKGROUND OF THE INVENTION

The present invention relates to a stone disintegrator apparatus and, more particularly, to a stone disintegrator apparatus utilizing an impulse spark.

A discharge stone disintegrator apparatus disintegrates stone with the shock wave resulting from an impulse spark generated between electrodes of a probe upon application of a high voltage thereto. In such a stone disintegrator apparatus, probe electrodes are worn with each spark discharge. Discharge impulse is attenuated as the discharge operation is repeated over again until finally, no discharge can be performed. In view of this, after the probe is used for a predetermined period of time, it is replaced. When the probe is replaced, conventionally, the discharge start voltage between the electrodes is detected, and the degree of wear of the electrodes with each use is determined from the detected voltage. When it is determined that the probe has worn too much, it is replaced.

In order to determine the time for replacing the probe, a voltage detector with a very high impedance must be inserted between the probe electrodes. However, such a voltage detector is susceptible to noise. Therefore, measurements taken by the detector tend to be incorrect, and time for replacing of the probe cannot be determined accurately.

SUMMARY OF THE INVENTION

It is an object of the present invention to provide a stone disintegrator apparatus wherein the number of discharge or probe operations is counted and the life of the probe is determined in accordance with the count.

According to the present invention, a stone disintegrator apparatus comprises a power supply section for applying a voltage to discharge electrodes of a probe, causing them to discharge, a life detection section for counting the number of discharge or probe operations and determining the life of the probe from the obtained count, and a re-use inhibit function section for inhibiting use of the probe in accordance with the life detection result by the life detection section.

BRIEF DESCRIPTION OF THE DRAWINGS

FIG. 11 is a circuit diagram of the apparatus using the plug shown in FIG. 9;

FIG. 12 is a front view of the apparatus shown in FIG. 11;

FIG. 13 is a perspective view of a probe plug used in a stone disintegrator apparatus in accordance with still another embodiment of the present invention;

FIG. 14 is a circuit diagram of a stone disintegrator apparatus having resistors each of which is fused for each predetermined number of discharge operations of the probe, in accordance with still another embodiment of the present invention;

FIG. 15 is a circuit diagram of the resistor unit used in FIG. 14;

FIG. 22 is a circuit diagram of a probe used in a stone disintegrator apparatus in accordance with still another embodiment of the present invention;

FIG. 23 is a circuit diagram of the probe shown in FIG. 22, when its life is ended;

FIG. 24 is a circuit diagram of a stone disintegrator apparatus in which a discharge tube for discharge voltage detection is connected to a probe in accordance with still another embodiment of the present invention;

FIG. 25 is a graph showing the relationship between the number of discharge operations and the discharge voltage;

FIG. 26 is a partial circuit diagram of a stone disintegrator apparatus having a memory for storing the number of discharge operations and a switching element for switching a discharge circuit in accordance with still another embodiment of the present invention;

FIG. 27 is a partial circuit diagram of a stone disintegrator apparatus having a discharge current detector, a memory and a discharge circuit switching element in accordance with still another embodiment of the present invention;

FIG. 45 is a circuit diagram of a life detection section using a memory storing the number of discharge operations in accordance with still another embodiment of the present invention;

FIG. 46 is a circuit diagram of a life detection section having a probe with a memory for storing the number of discharge operations and a number display in accordance with still another embodiment of the present invention;

FIGS. 47 and 48 are diagrams of a probe connector used in still another embodiment of the present invention; and FIG. 49 is a sectional view of a probe connector of used in still another embodiment of the present invention.

FIG. 50 is a partially sectional side view of a connector and a socket of a probe used in a stone disintegrator apparatus in accordance with still another embodiment of the present invention;

FIG. 51 is a partially sectional side view of the connector and socket shown in FIG. 50, which are coupled to each other;

FIG. 52 is a partially sectional side view of the connector and socket shown in FIG. 51, in which the connector is disconnected from the socket;

DETAILED DESCRIPTION OF THE PREFERRED EMBODIMENTS

Figure 1:
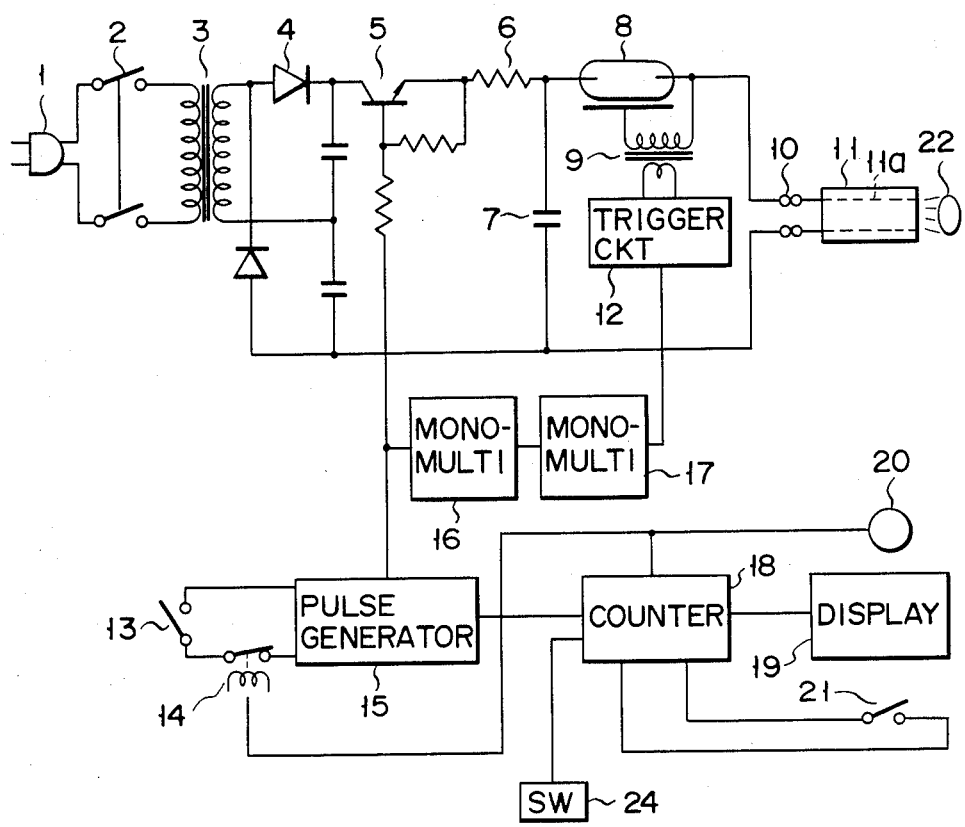
FIG. 1 is a circuit diagram of a stone disintegrator apparatus according to an embodiment of the present invention.

In an embodiment shown in FIG. 1, power supply plug 1 is connected to transformer 3 through switch 2. The secondary winding of transformer 3 is connected to transistor switch circuit 5 through booster/rectifier 4. The output terminal of circuit 5 is connected to capacitor 7 and discharge tube 8 through resistor 6. Trigger transformer 9 is connected to the trigger electrode of tube 8. The output section of tube 8 is connected to discharge electrodes 11a of probe 11 through socket 10. Trigger circuit 12 is connected to trigger transformer 9.

Discharge start switch 13 is connected to pulse generator 15 through relay 14. An output terminal of pulse generator 15 is connected to transistor circuit 5 and monostable multivibrator 16. The output terminal of multivibrator 16 is connected to trigger circuit 12 through another monostable multivibrator 17.

Another output terminal of pulse generator 15 is connected to counter 18. Counter 18 counts the number of discharge operations performed in accordance with output pulses from pulse generator 15. Counter 18 has an output terminal for generating a count and another output terminal for generating an output when the count reaches a predetermined value. The count output terminal of counter 18 is connected to display 19 and the predetermined value output terminal is connected to reset switch 21 and set switch 24.

Figure 2:
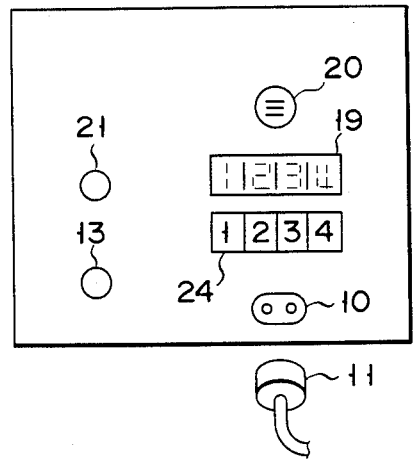
FIG. 2 is a front view of the apparatus in FIG. 1.

FIG. 2 shows the control panel of a discharge disintegrator apparatus of the present embodiment. The panel has connector 10, discharge start switch 13, display 19, buzzer 20, reset switch 21, and set switch 24. Probe 11 is connected to socket 10.

Figure 3:
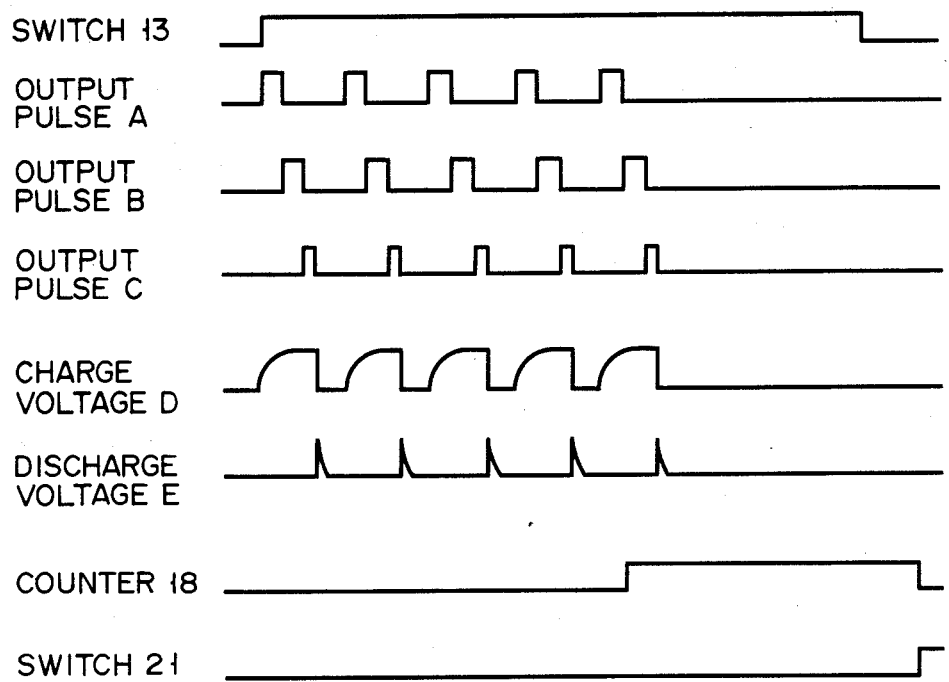
FIG. 3 is a timing chart for explaining the mode of operation of the apparatus in FIG. 1.

The operation of the apparatus will be described with reference to the timing chart shown in FIG. 3.

When switch 2 is turned on, booster/rectifier 4 outputs a high voltage. When switch 13 is turned on, pulse generator 15 generates pulse A, having a predetermined period. When circuit 5 is turned on in response to pulse A, the high voltage from booster/rectifier 4 is applied to capacitor 7 and capacitor 7 is charged to voltage D.

Pulse A is also supplied to trigger circuit 12 through monostable multivibrators 16 and 17. Multivibrator 16 generates pulse B in response to the trailing edge of pulse A while multivibrator 17 pulse C in response to the trailing edge of pulse B. When pulse C is supplied to trigger circuit 12, tube 8 is triggered. Thus, tube 8 is turned on a predetermined period of time after transistor circuit 5 is turned off. Transistor circuit 5 and tube 8 will not be simultaneously turned on.

When tube 8 is triggered, the charge voltage D of capacitor 7 is discharged through tube 8 and high voltage E is applied to electrodes 11a of probe 11. An impulse generated upon application of high voltage E causes discharge to occur at the distal end of probe 11, and stone 22 is disintegrated with the shock wave resulting therefrom. Pulse A of pulse generator 15 is also supplied to counter 18. The count of counter 18 is displayed on display 19. Counter 18 is preset to a predetermined value corresponding to the life of the discharge probe by set switch 24. When the count of counter 18 reaches the preset value, counter 18 supplies an output to relay 14 and buzzer 20. Relay 14 is energized in response to the output signal from counter 18 to stop oscillation of pulse generator 15. Buzzer 20 produces a sound to warn an end of life of the probe.

The life of probe 11 is roughly determined in accordance with the usual number of discharge operations per probe. This predetermined number of operations is set in counter 18, thus automatically determining the number of uses probe 11 will be subject to.

When pulse generator 15 stops oscillating, high voltage E is no longer supplied to probe 11, and probe 11 does not discharge. The operator confirms the life of probe 11 has expired by referring to the displayed number of operations or to the sound of buzzer 20. When probe 11 is replaced, reset switch 21 is operated and counter 18 is reset. Display 19 is reset to display "oooo" and buzzer 20 is stopped. Relay 14 is deenergized and the normally closed contacts are closed. In this state, the discharge stone disintegrator apparatus is again operative.

Figure 4:
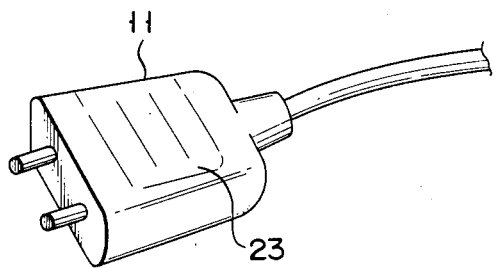
FIG. 4 is a perspective view of the plug of a probe.

When probe 11 is used within a short period of time after replacement, the number of discharge operations counted by counter 18 runs out before the actual life of probe 11. Therefore, the number of probe-operations, i.e., the number of discharge operations is confirmed by display 19. Th number of discharge operations is recorded on recording paper 23 attached to the plug of probe 11, as shown in FIG. 4. When probe 11 is used again, value "1177", e.g., obtained by subtracting the number of discharge operations recorded on recording paper 23, i.e., "57" from the life "1234" is set in counter 18 by set switch 24. Thereafter, the life is set to be 1177 and the operational state of probe 11 is again accurately monitored.

Figure 5:
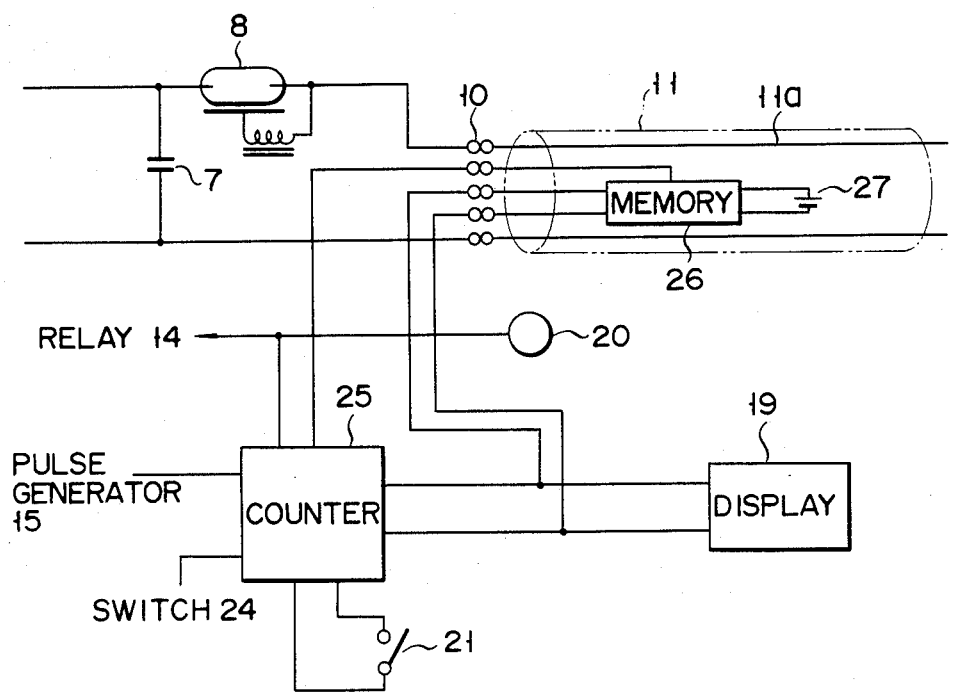
FIG. 5 is a circuit diagram of a stone disintegrator apparatus having a memory for storing data on the number of discharge operations performed in accordance with another embodiment of the present invention.

In accordance with another embodiment of the present invention shown in FIG. 5, counter 25 for counting pulses A is a counter which allows a count start value therein. Probe 11 has memory 26 backed up with battery 27.

In the above apparatus, the count of counter 25 is supplied to display 19 and memory 26, where it is stored. The count stored in memory 26 is compared with the count of counter 25. No change occurs if the two counts are the same.

When new probe 11 is mounted on the disintegrator and the life of new probe 11 is different from the count of counter 25, counter 25 is updated in accordance with the contents of memory 26. Counter 25 starts counting from the updated number of discharge operations, and the count result is supplied to display 19 and memory 26. In this embodiment, the contents of the counter are updated in accordance with the number of operations of the probe. Thus, the number of discharge operations performed is monitored.

Figure 6:
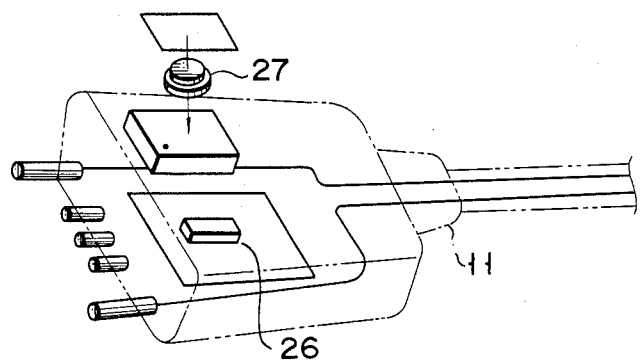
FIG. 6 is a perspective view of a probe plug used in the apparatus of FIG. 5.

Memory 26 and battery 27 of probe 11 are built into the plug of prove 11 as shown in FIG. 6.

Figure 7:
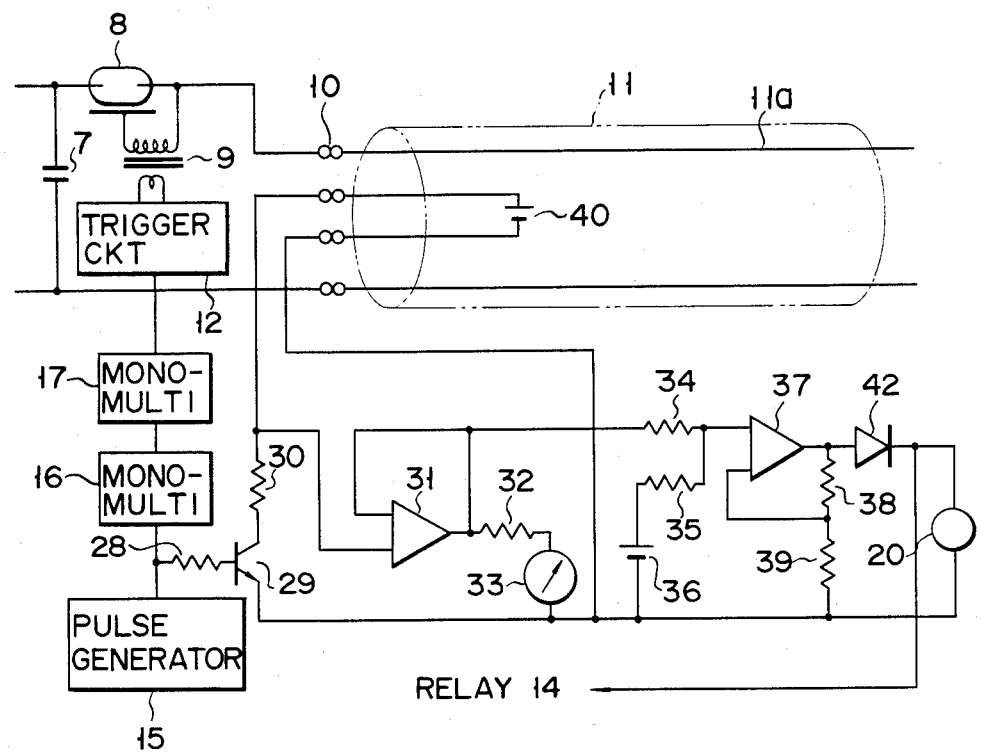
FIG. 7 is a circuit diagram of a stone disintegrator apparatus utilizing battery discharge in accordance with still another embodiment of the present invention.

In another embodiment shown in FIG. 7, the output terminal of pulse generator 15 is connected to the base of transistor 29 through resistor 28. The collector of transistor 29 is connected to the positive terminal of battery 40 in probe 11 through resistor 30 and to one input terminal of operational amplifier 31. The output terminal of operational amplifier 31 is connected to the emitter of transistor 29 through resistor 32 and meter 33, and to the negative terminal of battery 40 of probe 11. The output terminal of operational amplifier 31 is also connected to its other input terminal and to one input terminal of operational amplifier 37 through resistor 34. The same input terminal of amplifier 37 is connected to the emitter of transistor 29 through reference voltage source (battery) 36 and resistor 35. The output terminal of operational amplifier 37 is connected to the negative terminal of battery 36 through a series circuit of resistors 38 and 39 and to relay 14 and buzzer 20 through diode 42.

Figure 8:
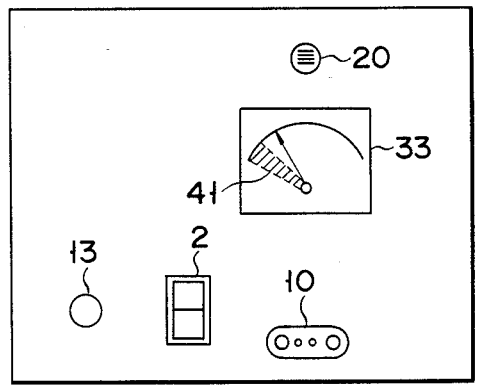
FIG. 8 is a front view of the apparatus of FIG. 7.

With the above arrangement, when each time pulse A is generated by pulse generator 15, i.e., each time a discharge is performed, transistor 1 is turned on and battery 40 of probe 11 discharges. Thus, as the number of discharge operations of probe 11 increases, the voltage of battery 40 is decreased. The battery voltage is displayed on meter 33 through a buffer comprising operational amplifier 31. The scale of the meter corresponds to the number of discharge operations and thus the number of discharge operations can be determined by reading the scale. Zone 41 corresponding to the life of probe 11 is marked in meter 33 as shown in FIG. 8. When the reading of meter 33 corresponds to zone 41, it is determined that the life of probe 11 has ended.

The output from buffer 31, i.e., the voltage of battery 40 is compared by a comparator comprising operational amplifier 37 with a reference voltage. When the voltage of battery 40 reaches the reference voltage, buzzer 20 produces a sound, relay 14 is energized, and probe 11 cannot discharge.

Figure 9:
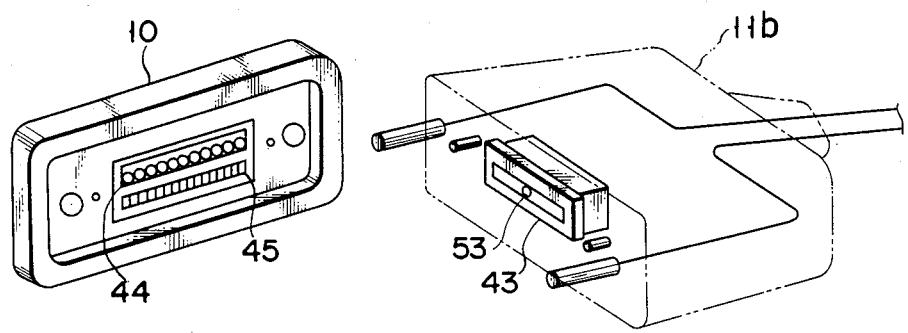
FIG. 9 is a perspective view of a plug and a socket used in another embodiment of the present invention.
Figure 10:
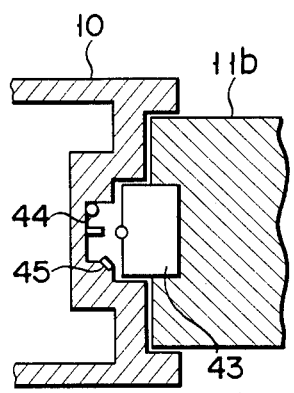
FIG. 10 is a sectional view of the plug and socket of FIG. 9, which are coupled to each other.

In an embodiment shown in FIG. 9, light-emitting element (light-emitting diode) array 44 and light-receiving element (solar cell) array 45 are arranged parallel to each other horizontally in socket 10 with elements therein opposed vertically. The number of elements in each array is the same and corresponding elements of the arrays face each other. Electrolytic integrating meter 43 is arranged in plug 11b of probe 11. When meter 43 is energized, it electrochemically integrates the power and displays the integrated value with display mark 53. When probe plug 11b having meter 43 is connected to socket 10, display mark 53 is interposed between arrays 44 and 45, as shown in FIG. 10.

As shown in FIG. 11, transistor 48 is connected to pulse generator 15 through resistor 46. The emitter of transistor 48 is connected to the cathode of array 44 and to the negative terminal of battery 49. The collector of transistor 48 is connected to meter 43 through resistor 47. The po itive terminal of battery 49 is connected to the anode of array 44 through resistor 54 and to meter 43.

The respective elements of array 45 are connected to corresponding elements of light-emitting diode array 52 through corresponding amplifiers of current amplification circuit 50 and resistors 51. Array 52 is mounted on the panel of the stone disintegrator as shown in FIG. 12.

In the discharge stone disintegrator apparatus described above, each time a pulse is generated by pulse generator 15, transistor 48 is turned on and a current from battery 49 flows into meter 43. Upon supply of this current, display mark 53 of meter 43 shifts to indicate the updated number of discharge operations. Display mark 53 is photoelectrically detected by arrays 44 and 45. In other words, display mark 53 is detected by the light-emitting and light-receiving elements corresponding to its position. The output from the specific light-receiving element drives the corresponding diode of array 52 through the corresponding amplifier and resistor. The number of discharge operations performed can be determined from the ON diode of array 52 on the apparatus panel and the remaining life of probe 11 can thus be confirmed. When a diode corresponding to the probe life expiration value is turned on, buzzer 20 produces a sound and relay 14 is deenergized to inhibit discharge.

In another embodiment shown in FIG. 13, meter 43 can be observed from the outside of probe plug 11b. Battery 49 is built in probe plug 11b. With this arrangement, the number of discharge operations can be confirmed by directly reading meter 43.

In another embodiment shown in FIG. 14, probe 61 comprises a flexible member. A pair of discharge electrodes 62a and 62b are mounted at the distal end of probe 61. Electrodes 62a and 62b are electrically connected to terminals 63a and 63b arranged at the proximal end of probe 61. Resistor unit 64 is also arranged at the proximal end of probe 61, its two ends being connected to terminals 63c and 63d. Probe 61 is detachably connected to the stone disintegrator apparatus.

AC power supply 65 is connected to primary winding 67a of transformer 67 through switch 66. Secondary winding 67b of transformer 67 is connected to charge/discharge circuit 69 through diode bridge rectifier 68. In response to a discharge command signal received from controller 71 comprising, e.g., a CPU, charge/discharge circuit 69 produces a pulsed voltage. The output terminal of circuit 69 is connected to probe 61.

Secondary winding 67c of transformer 67 is connected to constant voltage circuit 70. The output terminal of circuit 70 is connected to controller 71. Controller 71 is also connected to discharge switch 72, light-emitting diode (LED) 73, resistor blowing circuit 74, and resistor detection circuit 75. Diode 73 is arranged to indicate the life of discharge electrodes 62a and 62b of probe 61.

Unit 64 includes a plurality of parallel resistors R1, R2, R3, R4 and R5 as shown in FIG. 15. Resistors R1, R2, R3, R4 and R5 are blowed at different voltages. Resistor blowing circuit 74 comprises a circuit which sequentially produces a voltage of different value, e.g., sequentially increased voltages in response to each disconnection command signal from controller 71. Circuit 75 detects the resistance of unit 64 of probe 61 through terminals 63c and 63d and supplies the detected resistance data to controller 71.

The operation of the embodiment shown in FIGS. 14 and 15 will now be described. When probe 61 is mounted on the stone disintegrator apparatus and switch 66 is turned on, charge/discharge circuit 69 charges the internal capacitor (capacitor 7 as shown in FIG. 1) and circuit 75 detects the resistance of unit 64 of probe 61. When switch 72 is depressed while the resistance of unit 64 is below a predetermined value, a discharge command signal is supplied to circuit 69 from controller 71. In response to the discharge command signal, circuit 69 turns on the internal discharge tube (discharge tube 8 in FIG. 1) to discharge the capacitor in a pulsed manner and to apply a pulse voltage. The pulse voltage is applied to discharge electrodes 62a and 62b through terminals 63a and 63b of probe 61. A discharge occurs between electrodes 63a and 63b to disintegrate stone. Discharge is generated each time switch 72 is turned on.

Each time a discharge command signal is generated, controller 71 uses its internal counter to count the number of discharge operations. When the count of the counter reaches a predetermined value, controller 71 supplies a disconnection command signal to circuit 74. In response to the disconnection command signal, circuit 74 supplies a resistor blowing voltage to unit 64. In unit 64, resistor R1, for example, is disconnected by the blowing voltage from circuit 74. Circuit 74 supplies to unit 64 a voltage which is increased each time a disconnection command signal is supplied. In this manner, resistors R1, R2, R3, R4 and R5 are sequentially disconnected. When the resistors are sequentially blowed and the resistance of unit 64 reaches a predetermined value, controller 71 flashes LED 73 in response to an output signal from circuit 75 and inhibits the discharge operation of circuit 69. The flashing of LED 73 signals the end of the life of the discharge electrodes, i.e., a need for replacing the probe.

When probe 61 is replaced, the resistance of new unit 64 is detected by circuit 75. The resistance of new unit 64 is lower than the predetermined value and LED 73 stops flashing. Thus, discharge can be resumed. When probe 61 is not connected to the connector of the stone disintegrator apparatus, circuit 75 detects an infinitely large resistance. Therefore, LED 73 flashes and discharge between the discharge electrodes cannot occur.

The blowing algorithm of resistors R1, R2, R3, R4 and R5 of unit 64 is determined, for example, as follows:

1. First resistor R1 is blowed at the sixth discharge operation after power on.

2. Resistors R2, R3, R4 and R5 are sequentially blowed at each 500th discharge operation after first resistor R1 is blowed.

3. When all the resistors are blowed, the life of the probe ends and a buzzer is activated.

Assume that the discharge electrodes of probe 11 have a life of 2,000 discharge operations under preset conditions. When the sixth discharge operation is performed after power on, resistor R1 is blowed. Thereafter, discharge is repeatedly performed. When the number of discharge operations reaches 500, resistor R2 is blowed. Thus, as the number of discharge operations reaches 1,000, 1,500, and 2,000, resistors R3, R4 and R5 are sequentially blowed. When resistor R5 is blowed, i.e., when the life of probe 61 ends, diode 73 flashes and the discharge operation is inhibited.

When the total number of discharge operations is less than 500, a resistor is blowed every time the power is turned on. Therefore, diode 73 flashes after five turn on operations.

Figure 16:
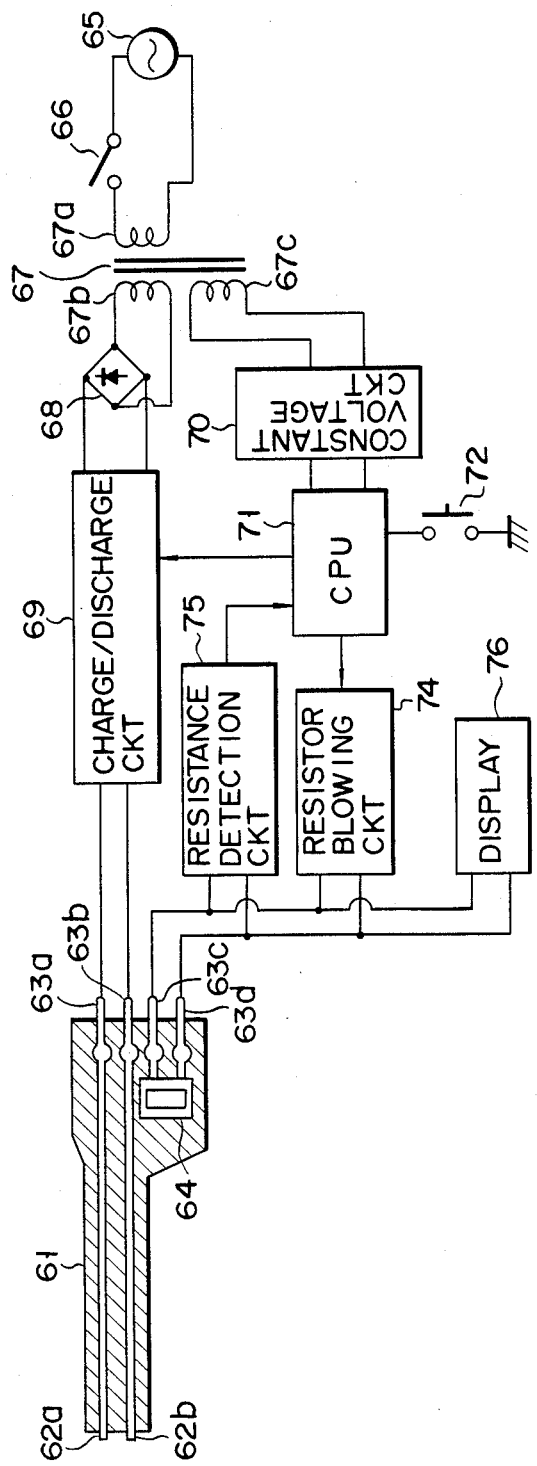
FIG. 16 is a circuit diagram of a stone disintegrator apparatus having a function of displaying the number of operations of the probe in accordance with still another embodiment of the present invention.
Figure 17:
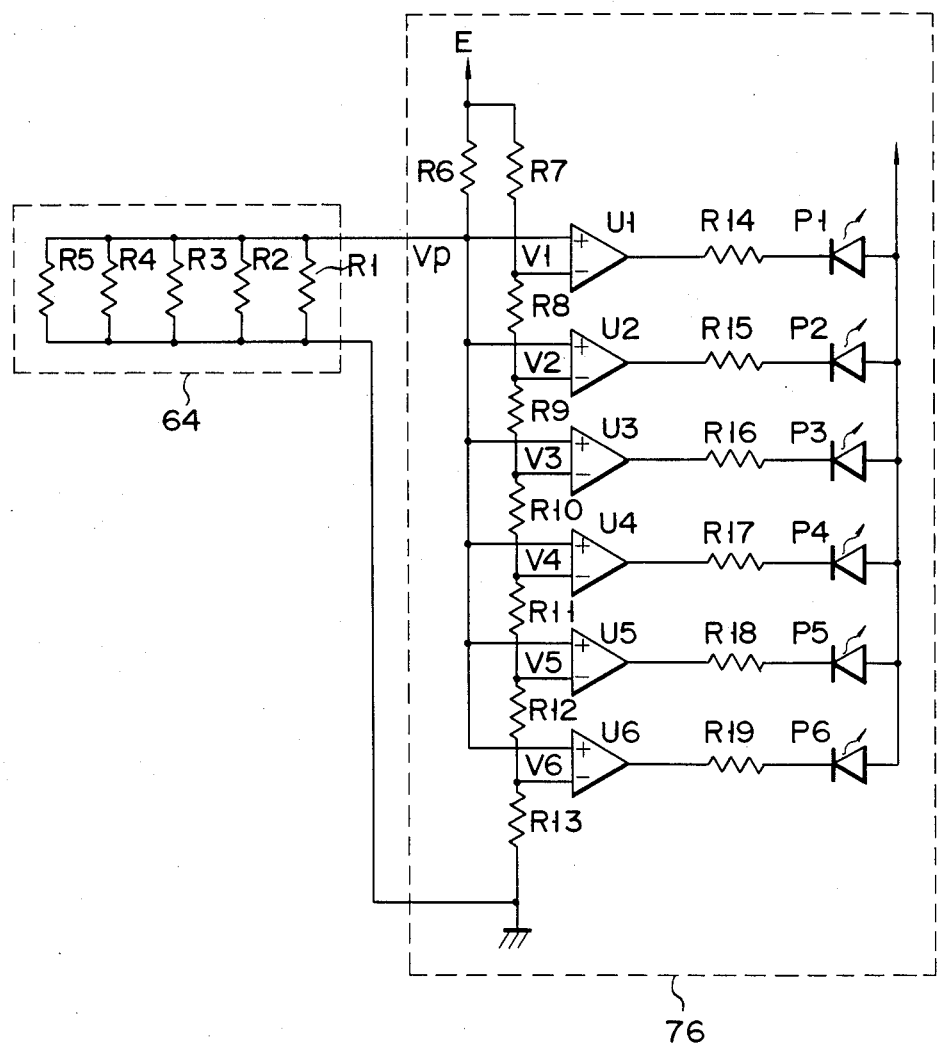
FIG. 17 is a circuit diagram of a display circuit used in the apparatus shown in FIG. 16.

FIG. 16 shows another embodiment of the present invention. In this embodiment, display circuit 76 is connected to resistor unit 64. FIG. 17 shows the circuit configuration of display circuit 76 and resistor unit 64. As shown in the circuit in FIG. 17, one output terminal of resistor unit 64, including parallel resistors R1, R2, R3, R4 and R5, is connected to power source E through resistor R6 of display circuit 76, and the other end thereof is connected to resistor R13 and to a reference potential, i.e., ground. Power source E is connected to resistor R13 through a series circuit of resistors R7 to R12. Nodes of resistors R7 to R12 are respectively connected to the inverting input terminals of comparators U1 to U6. The non-inverting input terminals of comparators U1 to U6 are connected to power source E through resistor R6. The output terminals of comparators U1 to U6 are connected to LEDs P1 to P6 through resistors R14 to R19, respectively.

With the above-described circuit connection, reference voltages V1 to V6 are respectively supplied to the inverting input terminals of comparators U1 to U6. Voltage Vp is a voltage appearing at the output terminal of probe 61, i.e., a voltage proportional to the output resistance of resistor unit 64. Voltage Vp is given by the following equation.

$$Vp = E \cdot Rp/(Rp+R6)$$

Rp: the output resistance of the probe

In the embodiment shown in FIG. 16, when power source switch 66 is turned on and discharge switch 72 is turned on while the output resistance of resistor unit 64 is less than a predetermined value, controller 71 supplies a discharge command signal to charge/discharge circuit 69. Discharge electrodes 62a and 62b of probe 61 start discharge in response to the signal. The number of discharge operations is counted by an internal counter of controller 71. When the count reaches a predetermined value, controller 71 supplies a disconnection command signal to resistor blowing circuit 74. In response to the disconnection command signal, circuit 74 supplies a resistor blowing voltage to resistor unit 64. Output resistance Rp1 of resistor unit 64 when none of resistors R1 to R5 is blowed is given by:

Rp1=R1//R2//R3//R4//R5

Output voltage Vp1 appearing at the output terminal of probe 61 in this state is given by:

$Vp1 = E \cdot Rp1/(Rp1+R6)$

Since voltage Vp1 is set to satisfy Vp1<V6<V5<V4<V3<V2<V1<E, all LEDs P1 to P6 are turned on.

If probe 61 has been used twice and resistors R1 and R2 of resistor unit 64 have been blowed, output resistance Rp2 of resistor unit 64 in this case is given by:

Rp2=R3//R4//R5

Voltage Vp2 appearing at the output terminal of probe 61 in this case is given by:

$Vp2 = E \cdot Vp2/(Rp2+R6)$

Since voltage Vp2 is set to satisfy V6<V5<Vp2<V4<V3<V2<V1<E, LEDs P1 to P4 are turned on and LEDs P5 and P6 are turned off. Thus, turning off of LEDs P4 and P6 indicates that the probe has been used twice.

As described above, resistors R1 to R5 of resistor unit 64 are sequentially blowed in accordance with the number of operations of probe 61, and initially ON LEDs P1 to P6 are sequentially turned off every time one of resistors R1 to R5 is turned off. When all resistors R1 to R5 are blowed, only LED P1 is turned on, and remaining LEDs P2 to P6 are turned off. If LED P1 emits red light and remaining LEDs P2 to P6 emit green light, the number of operations can be confirmed by counting the number of green ON LEDs and inhibition of discharge operation can be confirmed by the red ON LED.

In the embodiment shown in FIG. 16, if the life of the discharge electrodes in a probe is 2,000, all resistors R1 to R5 are blowed upon completion of 2,000 discharge operations and the probe can n longer be used. When the number of discharge operations is less than 500, one resistor is blowed each time the power is turned on and 6 discharge operations are performed. Therefore, only LED P1 is turned on after 5 power on operations, and it indicates that the probe cannot be used.

In the embodiment shown in FIG. 16, the number of LEDs which are turned on, corresponds to the number of non-disconnected resistors. However, one LED corresponding to an output resistance at the time of measurement can be turned on. In addition, in the above embodiment, a light-emitting diode is used as a means for signalling the end of probe life. However, a buzzer or an alarm sound generating unit can also be used.

Figure 18:
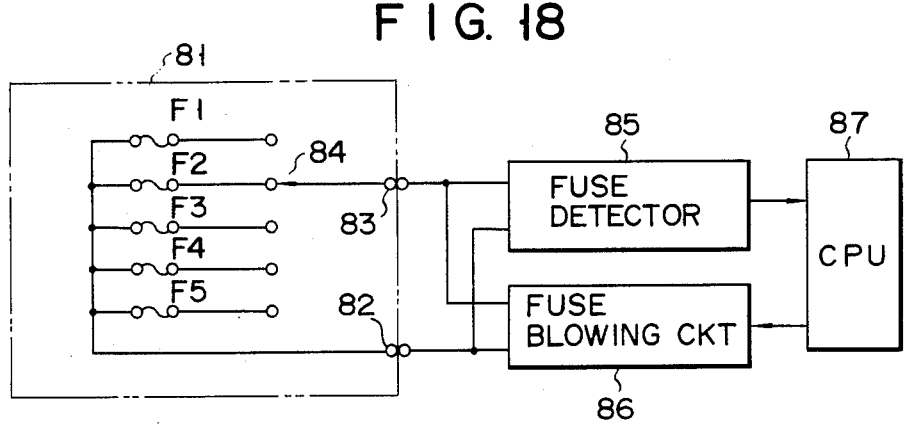
FIG. 18 is a circuit diagram of a fuse unit and a life detector used in a stone disintegrator apparatus in accordance with still another embodiment of the present invention.

In another embodiment shown in FIG. 18, fuse unit 81 is arranged in a probe. Fuse unit 81 has a plurality of fuses F1 to F5. One end of each fuse is connected to terminal 82, and the other end is connected to one of the contacts of switch 84. The common contact of switch 84 is connected to terminal 83. When the stone disintegrator apparatus of this embodiment is connected to a probe plug, terminals 82 and 83 of fuse unit 81 are connected to fuse detector 85 and fuse blowing circuit 86.

In the embodiment shown in FIG. 18, assume that fuse F1 of fuse unit 81 is blowed and switch 84 is switched to fuse F2. When the power of the stone disintegrator is turned on in this state, fuse detector 85 detects fuse F2 of fuse unit 81. When fuse F2 is not blowed, it is determined that the probe can be used and stone disintegration can be performed. When stone disintegration is performed, fuse blowing circuit 86 supplies a fuse blowing current to fuse F2, blowing it. Thereafter, stone disintegration is continued until the power is turned off.

When power is turned on again after having been turned off once, fuse detector 85 detects fuse F2. In this case, since fuse F2 is disconnected, it is determined that the probe cannot be used. In this case, switch 84 is switched to fuse F3, detector 85 detects fuse F3, and the probe can be used. In this manner, every time power is turned on, a fuse is blowed and switch 84 moves to a new fuse. When fuse F5 is blowed and this disconnection is detected by fuse detector 85, it is determined that the life of the probe having this fuse unit has come to an end.

Figure 19:
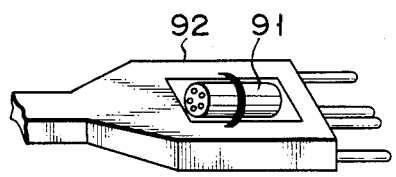
FIGS. 19 to 21 are perspective views of various plugs of the probe used in the embodiment of FIG. 18.
Figure 20:
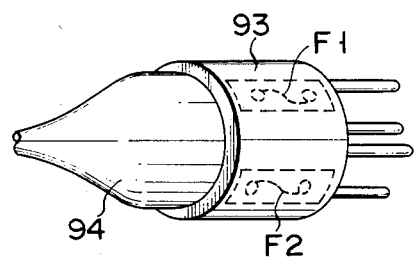
Figure 21:
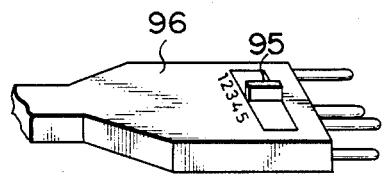

The fuses of fuse unit 81 can be switched by a means shown in FIGS. 19 to 21. In the arrangement shown in FIG. 19, fuse cylinder 91 housing fuses F1 to F5 is rotatably mounted in plug 92. Fuse cylinder 91 is rotated by a hand when fuses are replaced.

In the arrangement shown in FIG. 20, cylinder 93 housing fuses F1 to F5 is rotatably fitted around connector 94. Cylinder 93 is rotated by hand so as to sequentially switch fuses F1 to F5.

In the arrangement shown in FIG. 21, slide switch 95 is mounted on connector 96, and fuses F1 to F5 are connected to the contact of slide switch 95. Fuses F1 to F5 are sequentially switched when slide switch 95 is moved from 1 to 5, respectively.

Referring to FIGS. 19 to 21, fuse cylinder 91, cylinder 93 and slide switch 95 are irreversible. When such switching members are reversible, the following problem occurs. For example, assume after fuse F1 is switched to fuse F2 upon blowing of fuse F1 and fuse detector 85 detects non-disconnection of fuse F2, the switching member is returned to fuse F1. In this case, since fuse F2 is never blowed, the probe can be permanently used.

In another embodiment shown in FIG. 22, connector pin 101a of a probe is connected to contact 102. Contact 102 is connected to paraffin member 104 by connection lever 103. Contact 102 is also connected to contact 105. Contact 105 is connected to one discharge electrode 107a through stopper 106 comprising a resistor element and contacting paraffin member 104. The other discharge electrode 107b is connected to connector pin 101b.

Current is supplied to resistor stopper 106 and stopper 106 is heated every time a discharge current is supplied to the probe through connector pins 101a and 101b and discharge occurs between discharge electrodes 107a and 107b. Paraffin member 104 is partially fused by the heat from the stopper 106. Since paraffin member 104 is urged against stopper 106 by lateral force of spring 108 acting from the side of contact 102, paraffin member 104 is deformed by heat generated by stopper 106 upon every discharge. When a predetermined number of discharge operations are performed, paraffin member 104 is deformed by the heat of stopper 106 in such a way that member 104 is disengaged from stopper 106 and contact 102 is disconnected from contact 105, as shown in FIG. 23. Therefore, no more current is supplied to discharge electrodes 107a and 107b of the probe, and discharge cannot be performed. In the embodiment shown in FIG. 22, paraffin member 104 and stopper 106 serve as a discharge electrode life detector, and the end of probe life can be detected thereby.

In another embodiment shown in FIG. 24, discharge tube 110 is connected between discharge electrodes 111a and 111b of a probe. In general, as the number of discharge operations between discharge electrodes 111a and 111b increases, the gap between electrodes 11a and 11b increases due to electrode wear. For this reason, a discharge start voltage is increased in proportion to the electrode gap.

FIG. 25 shows the relationship between the number of discharge operations and the discharge start voltage. Referring to FIG. 25, curve indicates the interelectrode discharge start voltage, and curves b and c respectively indicate the discharge voltage of discharge tube 110 and the charge voltage of capacitor 112. When discharge tube 113 is turned on by a trigger pulse from trigger circuit 114 and a charge voltage of capacitor 112 is applied to discharge tube 110 and discharge electrodes 111a and 111b, if the discharge start voltage is less than the discharge voltage of discharge tube 110, electrodes 111a and 111b discharge. However, if the discharge start voltage exceeds the discharge voltage of discharge tube 110, the voltage applied by capacitor 112 is bypassed by discharge tube 110. Thus, an end of probe electrode life is detected.

In another embodiment shown in FIG. 26, a probe has memory 121 for storing the discharge number data in a discharge stone disintegrator, e.g., the count of counter 18 shown in FIG. 1. Memory 121 is connected to switch drive circuit 122. Circuit 122 has a comparator and a driver. The comparator compares data representing an actual discharge number from memory 121 with reference data representing a predetermined discharge number (the number of discharge operations corresponding to the electrode life). The driver produces a drive signal in response to an output from the comparator. When transistor 123 is turned off by the drive signal, the discharge circuit of the stone disintegrator is opened. In other words, discharge operation is inhibited.

In a probe shown in FIG. 27, discharge current flowing through discharge electrodes 124a and 124b is detected by current detection transformer 125. The current detected by transformer 125 is stored in analog memory 121. The memory content of analog memory 121, i.e., the actual discharge operation number data is compared with reference data of switch drive circuit 122. Switch transistor 123 is turned off by a drive signal from circuit 122, thus inhibiting further discharge operations.

Figure 28:
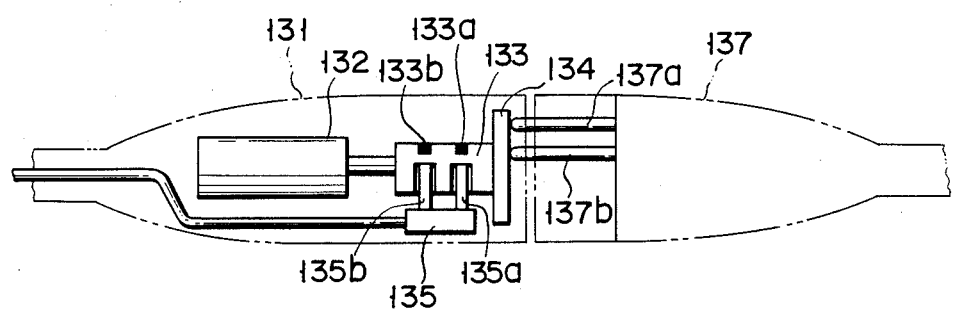
FIG. 28 is a diagram showing the construction of a probe connector used in a stone disintegrator apparatus in accordance with still another embodiment of the present invention.
Figure 29:
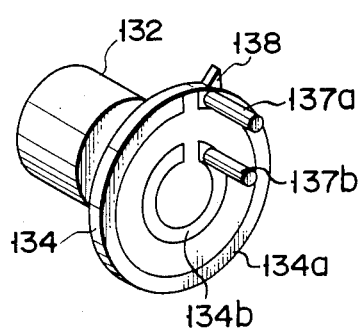
FIG. 29 is a perspective view of a life detection section arranged in the connector, shown in FIG. 28, and using a motor.

In another embodiment shown in FIGS. 28 and 29, pulse motor 132 is arranged in probe connector 131. Rotary contact 133 is coupled to the shaft of pulse motor 132. Rotary plate 134 is mounted on the distal end of rotary contact 133. Contact pieces 133a and 133b in contact with brush 135 are arranged on contact 133. As shown in FIG. 29, rotary contact 133 has contact pieces 134a and 134b having a length corresponding to a life of the probe. Contact pieces 134a and 134b are in contact with contact pins 137a and 137b of connector 137 connected to a stone disintegrator. Contact pieces 133a and 133b and 134a and 134b are connected to each other, and are connected to the discharge electrodes through contacts 135a and 135b of brush 135.

Pulse motor 132 is driven by a drive pulse synchronised with discharge operation. The drive pulse can be obtained from a drive pulse generator which generates a pulse in synchronism with an output from monostable multivibrator 17 in the embodiment shown in FIG. 1. When pulse motor 132 is driven by a drive pulse, as motor 132 is rotated, rotary contact 133 and rotary plate 134 rotate. During rotation of plate 134, while contact pins 137a and 137b of connector 137 are in contact with contacts 134a and 134b of plate 134, discharge current flows to the discharge electrodes through pins 137a and 137b, pieces 134a, 134b, 133a and 133b, and contacts 135a and 135b. When contact pins 137a and 137b are located at the non-conductive portions of rotary plate 134, the discharge current path is cut off and discharge operation is inhibited.

Figure 30:
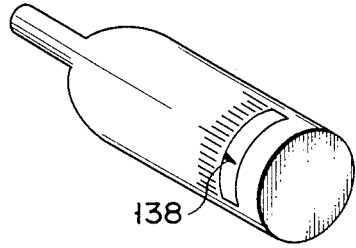
FIG. 30 is a perspective view of the connector shown in FIG. 28.

Pointer pin 138 mounted on plate 134 is moved therewith so as to indicate the number of discharge operations, as shown in FIG. 30.

Figure 31:
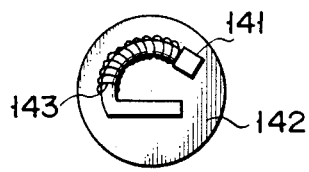
FIG. 31 is a back view of a life detection section using an electromagnetic plunger.
Figure 32:
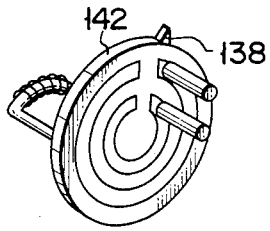
FIG. 32 is a perspective view of the life detection section using an electromagnetic plunger.

FIGS. 31 and 32 show another embodiment wherein a ratchet mechanism 141 is provided. In this embodiment, electromagnetic plunger 143 is arranged close to rotary plate 142. When plunger 143 is biased by a trigger pulse for starting discharge, ratchet mechanism 141 is actuated and plate 142 is rotated by one step. When plate 142 is sequentially rotated in accordance with operation of the ratchet mechanism, the number of discharge operations is measured and the electrode (probe) life is detected.

Figure 33:
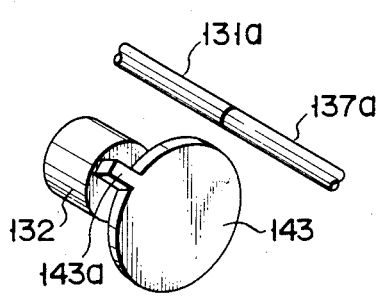
FIG. 33 is a perspective view of a life detection section arranged in a probe used in still another embodiment of the present invention.
Figure 34:
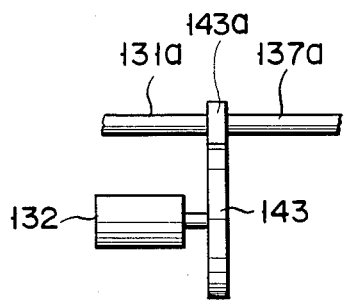
FIG. 34 is a side view of the life detection section shown in FIG. 33, when the life of the probe is ended.

In another embodiment shown in FIG. 33, insulating projection 143a is formed on rotary plate 143, coupled to the shaft of pulse motor 132. When rotary plate 143 is rotated to an angle corresponding to the life expectancy of the discharge electrodes, projection 143a is inserted between contact pin 131a and contact pin 137a of probe connector 137 (FIG. 34). In this state, discharge operation is inhibited, and the expired life of the discharge electrodes is detected.

Figure 35:
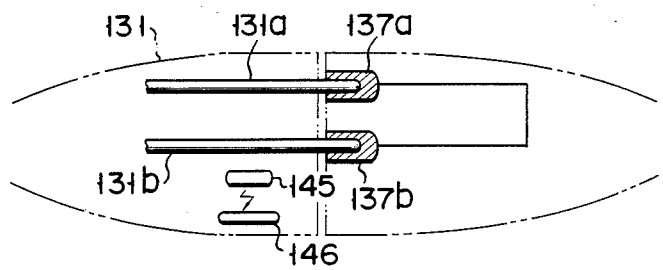
FIG. 35 is a diagram showing a probe connector having an LED and a photosensor in accordance with still another embodiment of the present invention.
Figure 36:
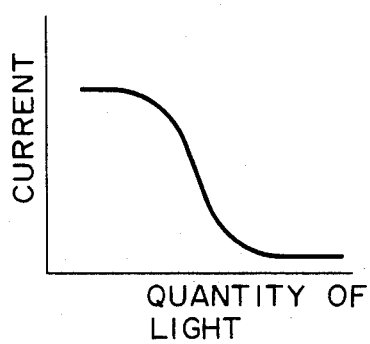
FIG. 36 is a graph showing the relationship between the LED light amount and current flowing through the photosensor.

In another embodiment shown in FIG. 35, probe connector 131 has light-emitting diode (LED) 145 and photosensitive film 146 sensitive to light from LED 145. Light from LED 145 is emitted synchronously with electrode discharging, and film 146 is exposed to the amount of light emitted by LED 145. As film 146 is exposed, its resistance increases. Therefore, when electrodes are connected to film 146 and a current is supplied to film 146 though the electrodes, the current changes in accordance with the quantity of light received by film 146, as shown in FIG. 36. Therefore, the number of discharge operations can be detected by detecting the current flow to film 146.

Figure 37:
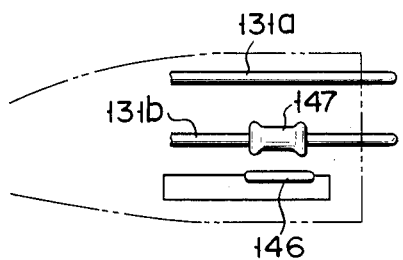
FIG. 37 is a diagram showing a probe connector having a life detection section with a photosensor and a heat generator in accordance with still another embodiment of the present invention.

In another embodiment shown in FIG. 37, heating resistor 147 is connected contact pin 131b of probe connector 131. Resistor 147 generates heat upon supply of discharge current to contact pin 131b and thus generates heat rays or infrared rays. Film 146 is exposed to the heat or infrared rays. The life of discharge electrodes is detected by detecting current flow to film 146, as in the embodiment shown in FIG. 35.

Figure 38:
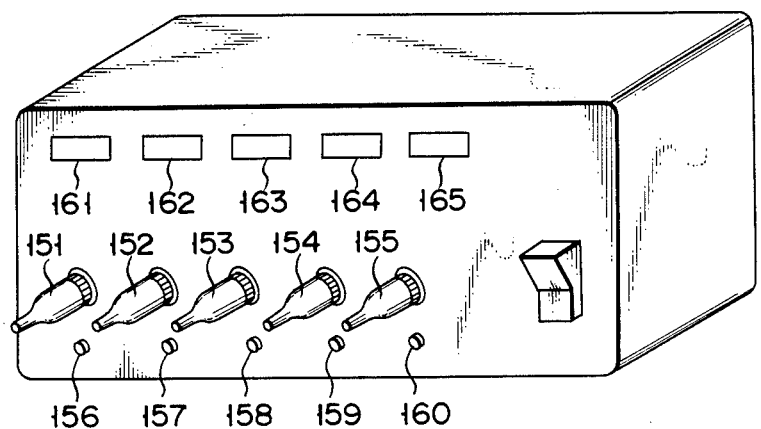
FIG. 38 is a perspective view of a stone disintegrator for checking the life of a plurality of probes.

In FIG. 38, a plurality of discharge probes 151 to 155 are connected to probe checker 150. Checker 150 checks the number of discharge operations and life of each probe. Probe checker 150 has discharge check switches 156 to 160 arranged at the lower portion thereof. Display panels 161 to 165 for displaying the number of discharge operations are arranged at the upper portion of checker 150. Probes 151 to 155 have memories for storing the number of discharge operations. Discharge number data in these memories are displayed on display panels 161 to 165. When discharge check switches 156 to 160 are turned on, corresponding probes can be checked.

Figure 39:
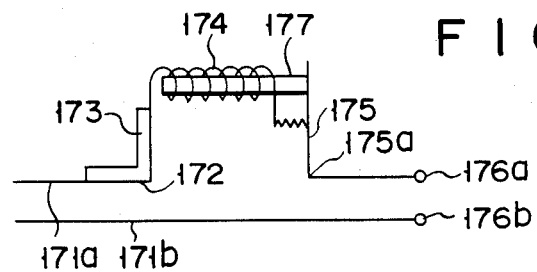
FIGS. 39 and 40 are diagrams of a life detection section arranged in various probes in accordance with still other embodiments of the present invention and utilizing the physical fatigue of a conductive member.

In another embodiment shown in FIG. 39, electrode line 171a of a probe is connected to one end of excitation coil 174 through conductor 172. Conductor 172 is reinforced by reinforcing member 173. The other end of coil 174 is connected to connector terminal 176a through bent conductor 175. Core 177 is mounted near one end of conductor 175 and is inserted in coil 174. Electrode line 171b is connected to connector terminal 176b.

Referring to FIG. 39, when discharge current is supplied between terminals 176a and 176b, coil 174 is energized and core 177 is moved. Movement of core 177 is transmitted to conductor 175 and applies a bending force to bent portion 175a of conductor 175. This bending force is produced every time coil 174 is energized. Therefore, as the number of discharge operations increases, bent portion 175a fatigues and finally fractures. Fracture of the conductor is an indication of the end of probe life.

Figure 40:
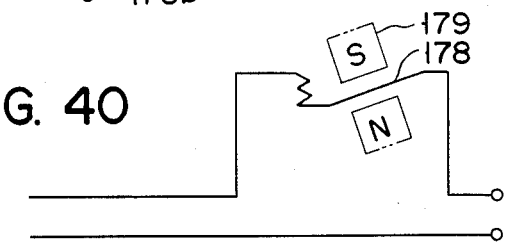

FIG. 40 shows a modification of the embodiment of FIG. 39. In the modification, conductor 178 is inserted between N and S poles of magnet 179. Every time discharge current flows to conductor 178, it oscillates in accordance with the left-hand rule of Faraday. Then, as discharge operation progresses, conductor 178 is subject to metal fatigue and finally fractures.

Figure 41:
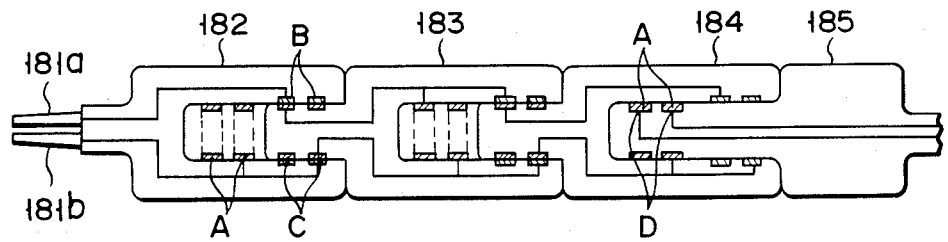
FIG. 41 is a sectional view of a probe having a plurality of connectors in accordance with still another embodiment of the present invention.

In another embodiment shown in FIG. 41, dummy conductors 183 and 184 and main connector 185 are sequentially connected to connector 182 having discharge electrodes 181a and 181b. In connectors 182 to 184, contacts A and B are arranged at recesses and contacts C are arranged on projections. Recessed contacts D are arranged at a projection of main connector 185.

When main connector 185 is connected to dummy connector 184, contacts A of connector 184 are fitted in recessed contacts D of connector 185. When main connector 185 is disengaged from connector 184, contacts A are removed from connector 184 by recessed contacts D of connector 185 and cannot be provided for the next use. Therefore, when the probe is used for the second time, main connector 185 is inserted into dummy connector 183. In this manner, since dummy connectors are sequentially switched for each operation of probe, the probe life can be determined from the number of remaining dummy connectors.

Figure 42:
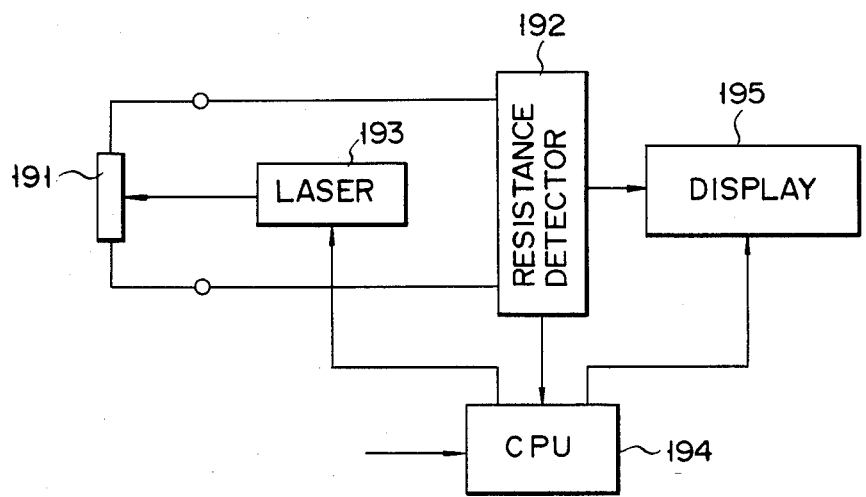
FIG. 42 is a circuit diagram of a life detection section using a laser in accordance with still another embodiment of the present invention.

In another embodiment shown in FIG. 42, resistor 191 is arranged in a probe. Resistor 191 is connected to resistance detector 192 for detecting the resistance of resistor 191. Laser 193 for resistor 191 is arranged in a stone disintegrator apparatus. Detector 192 and laser 193 are connected to CPU 194. Resistance detector 192 is connected to display 195 for displaying the resistance.

Figure 43:
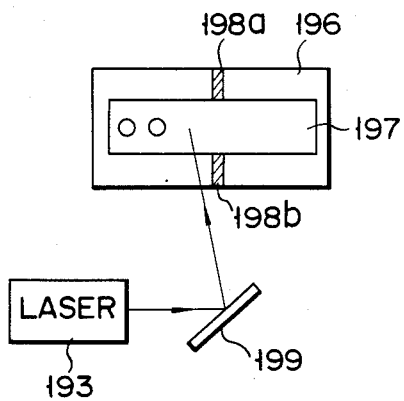
FIGS. 43 and 44 are diagrams of the life detection section shown in FIG. 42.

As shown in FIG. 43, resistor 191 includes substrate 196, resistor film 197 formed on the surface of substrate 196, and electrodes 198a and 198b on substrate 196. A laser beam from laser 193 is directed toward film 197 by movable mirror 199 and radiates film 197.

In the above construction, in response to discharge number data from a discharge number counter (e.g., counter 18 in FIG. 1), CPU 194 supplies a drive command to laser 193. In response to the command, laser 193 generates a laser beam to partially burn film 197 of resistor 191. The resistance of resistor 191 increases and is detected by resistance detector 192 through electrodes 198a and 198b. The detected resistance is displayed by display 195.

As described above, every time a predetermined number of discharge operations is performed, film 197 is burnt by a laser beam and the film resistance increases. When the resistance reaches a pedetermined value, CPU 194 determines that the probe life has ended and cuts off the discharge circuitry.

Figure 44:
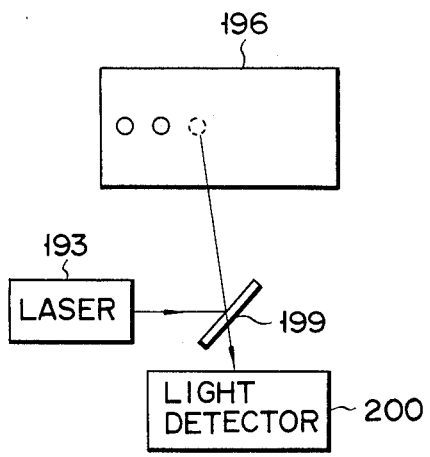

When laser 193 burns film 197, the laser beam must be scanned to a non-burnt portion. In this case, as shown in FIG. 44, a weak laser beam is radiated from laser 193 onto the surface of film 197. The weak laser beam is reflected by a plastic film coated on the surface thereof. When the reflected light is detected by photodetector 200 through half mirror 199, laser 193 produces a laser beam. When the weak laser beam scans a burnt portion and no reflected light is detected, half mirror 199 is moved to change the landing position of the laser beam. Since reflected light is detected at the new position, laser 193 then produces a laser beam.

In another embodiment shown in FIG. 45, memory 201 for storing the number of discharge operations or power on operations is provided. Memory 201 comprises, e.g., a fuse ROM, a NV (non-volatile) RAM, a battery back-up RAM, or a combination thereof with a ROM. A fuse ROM comprises, e.g., a number of fuses arranged in a matrix form. Data is written by selectively blowing these fuses. NV (non-volatile) RAM and battery back-up memories can protect data upon power failure.

Memory 201 is connected to CPU 203 through interface (IF) 202 of a stone disintegrator. When a fuse memory is used as memory 201, upon each discharge or power on operation, a signal is supplied to memory 201 through IF 202 and the corresponding fuse of the fuse memory is blowed. Thus, the life of discharge electrodes can be determined in accordance with the number of remaining fuses of the fuse memory. The life of discharge electrodes can be determined by monitoring the contents of memory 201 with CPU 203.

A NV (non-volatil) RAM or back-up memory RAM stores data to be supplied to memory 201 through IF 202 upon each discharge or power on operation. The stored data is supplied to CPU 203 through IF 202 to monitor the discharge electrode life. When CPU 203 determines that the life of the discharge electrodes has ended, CPU 203 cuts off the discharge circuitry and inhibits discharge by the probe.

If a program for generating a discharge pattern suitable for the particular probe in use is stored in memory 201, the probe can discharge in an optimal discharge pattern. When data representing a certain type of probe is stored, when a new probe is connected to the stone disintegrator, the probe can be matched against corresponding stored data.

In another embodiment in FIG. 46, a probe has CPU 203 and display 204 in addition to memory 201. In response to discharge operation number data or power on operation number data from stone disintegrator 100, CPU 203 stores the data in memory 201. When memory 201 is a fuse memory, a fuse disconnected signal is supplied as data to CPU 203, and a corresponding fuse of the fuse memory is blowed in response to the signal.

The stored contents of memory 201 are displayed by display 204 through CPU 203. In this case, the number of signal lines connecting the probe and stone disintegrator 100 can be reduced significantly.

In another embodiment shown in FIG. 47, the number of operations of probe is mechanically measured. Connection pins 301a and 301b are arranged inside probe plug 300. Counter unit 302 is arranged outside probe plug 300. Guide pin 303 is slidably arranged in counter unit 302. Counter drum 304 is rotatably arranged near slide pin 303. Numbers for indicating the number of probe-operations are marked around counter drum 304. Slide groove 305 is formed at one end of drum 304. Projection 303a formed on slide pin 303 is engaged with slide groove 305. The other end of counter drum 304 is elastically pressed by press member 306.

When probe plug 300 mounting counter unit 302 having the above arrangement is inserted into socket 307 of a stone disintegrator, projection 307a formed on socket 307 presses slide pin 303 of plug 300. At this time, projection 303a of slide pin 303 slides in groove 305 of counter drum 304 and rotates counter drum 304. Then, count number "1" appears in display window 302a of counter unit 302, as shown in FIG. 48. The number indicates that probe has been used once.

When stone disintegration ends and probe plug 300 is disengaged from socket 307, slide pin 303 is returned to the original position by the spring force. Then, counter drum 304 is rotatably held by engaging groove 304a formed at the other end of drum 104 and engaging pin 306a formed in press member 306.

When probe plug 300 is again inserted into socket 307, number "2" is displayed in display window 302a as above. In this manner, every time probe plug 300 is inserted into socket 307, the number indicated in window 302a is increased in unitary increments and indicates the number of operations of the probe. The probe life can be determined from the displayed number. When counter drum 304 rotates a number of times corresponding to the probe life expectancy, projection 304b, formed in drum 304, is inserted into recess 303b of slide pin 303. In this state, slide pin 303 cannot move, and the probe cannot be used.

In another embodiment shown in FIG. 49, slide pin 311 is slidably inserted at the central portion of counter drum 310. When slide pin 311 is pressed by projection 307a of socket 307 of a stone disintegrator, counter drum 310 rotates by mutual action of slide groove 310a formed in the inner surface of counter drum 310 and projection 311a of slide pin 311. Counter unit 302 thus counts the number of probe uses.

FIG. 50 shows still another embodiment of the present invention which uses a throw away probe. Axial cylinder hole 402 is formed in plug 401 of the probe. Cylinder hole 402 corresponds to pin 411 of socket 410 of a stone disintegrator. Piston 403 is slidably arranged in cylinder hole 402 and is biased outward by spring 404. Cross hole 405 is formed in probe plug 401 to extend perpendicularly to cylinder hole 402. Lock pin 406 is slidably arranged in hole 405. Lock pin 405 is biased toward piston 403 by spring 407.

When probe plug 401 shown in FIG. 50 is coupled to socket 410 shown in FIG. 51, piston 403 is pressed into cylinder hole 402 by socket 410. Then, piston 403 is removed from lock pin 406, and lock pin 406 is pressed into cylinder hole 402 by the biasing force of spring 407.

The probe is used in this state, and stone is disintegrated by discharge between discharge electrodes of the probe.

When stone disintegration ends, probe connector 401 is disconnected from socket 410. Then, lock pin 406 is inserted completely into cylinder hole 402, and cylinder hole 402 is closed by lock pin 406, as shown in FIG. 52. In this state, even if one attempts to reinsert plug 401 into socket 410, pin 411 of socket 410 abuts against lock pin 406 and does not allow coupling between plug 401 and socket 410. Therefore, the probe cannot be used and is disposed. In this manner, the probe having the connector as shown in FIG. 50 is a throw away probe which is discarded upon being used once.

Figure 53:
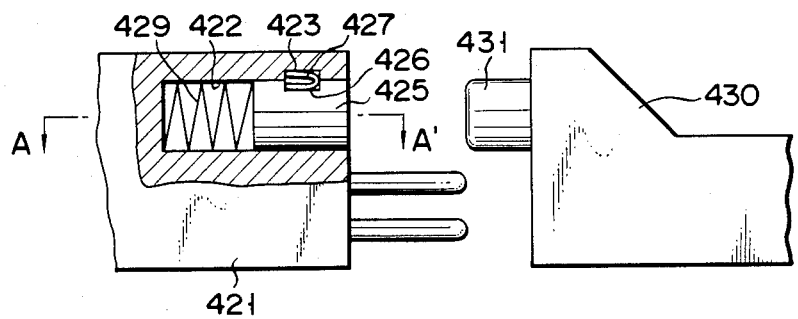
FIG. 53 is a partially sectional side view of a connector and socket of a probe of a stone disintegrator apparatus in accordance with still another embodiment of the present inventtion.
Figure 54:
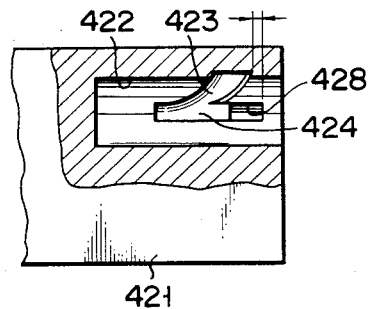
FIG. 54 is a partially sectional side view of the connector shown in FIG. 53.
Figure 55:
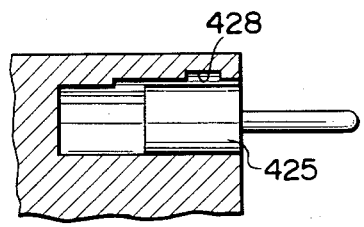
FIG. 55 is a sectional view of the connector along the line A—A' in FIG. 53.

FIG. 53 shows connector 421 of another throw away probe. Grooves 423 and 424 are formed in the inner wall of cylinder hole 422 formed in plug 421. Groove 423 extends helically about 90 degrees toward the cylinder hole bottom, and groove 424 extends straight to the outside and communicates with groove 423. The distal end of groove 424 extends slightly beyond that of groove 423. Step 428 is formed at the distal end of groove 424. Piston 425 is slidably inserted in cylinder hole 422. Groove 426 is formed in piston 425 to correspond to groove 423 of cylinder hole 422. Stopper spring 427 is inserted between grooves 426 and 423.

When connector 421 in FIG. 53 is coupled to socket 430, piston 425 of connector 421 is inserted into cylinder hole 422. Stopper spring 427 slides in groove 423 and rotates together with piston 425 about 90 degrees in cylinder hole 422.

Figure 56:
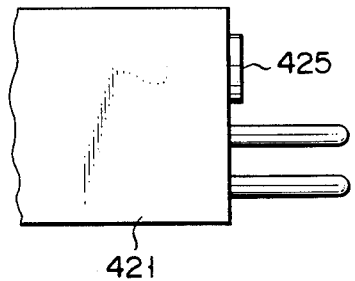
FIG. 56 is a side view of a connector of a used probe.

When connector 421 is securely coupled to socket 430, a discharge voltage is applied to the discharge electrodes to perform stone disintegration. When stone disintegration is completed and connector 421 is disconneced from socket 430, piston 425 is pressed out from hole 422 by spring 429. Stopper spring 427 moves along groove 424 and is fitted in step 428 at the end of groove 424. Cylinder 425 is locked by stopper spring 427 while its distal end is slightly exposed from the end face of connector 421. In this state, cylinder 425 cannot move. The probe cannot therefore be used and is disposed. In plug 421 of the used probe, piston 425 partially projects from the end face of connector 421 as shown in FIG. 56. Therefore, a used probe can be easily differentiated from a non-used probe.

In the stone disintegrator apparatus described above, the life of a discharge probe can be easily determined and problems occurring during stone disintegration due to defective probes can be prevented.

In order to prolong life of discharge electrodes, the electrodes are made of a material having a high electrical insulating property and a high heat resistance, e.g., ceramic or glass. The selected material is buried at probe tips such that the electrode surfaces are exposed. When a probe having such an arrangement is used, the probe tips will not be damaged due to heat generated between the electrodes and the probe life is prolonged.

What is claimed is:
1. A stone disintegrator apparatus comprising:
a probe having discharge electrodes;
power supply means for applying a discharge voltage to said probe in order to allow said discharge electrodes to discharge for disintegrating a stone;
detecting means coupled to the power supply means for establishing a service life of said probe from at least one of the number of discharges and the number of operations of said probe from its installation, and to generate an inhibit signal at the expiration of said service life; and means coupled to the detecting means for inhibiting use of said probe in response to said inhibit signal; wherein said probe comprises a resistor unit having a plurality of resistors which are fused at different voltages; said detecting means comprises resistance detecting means for measuring a resistance of said resistor unit and means for applying to said resistor unit different voltages for sequentially disconnecting said tesitors upon each predetermined number of discharge operation, said inhibit signal being generated in response to a predetermined measured value of said resistance detecting means; and said inhibiting means inhibits said power supply means to prevent use of the probe beyond said service life.

2. An apparatus according to claim 1, wherein said life detecting means comprises discharge count means for counting the number of discharge operations between said discharge electrodes, memory means for storing the number of discharge operations from said count means, and means for comparing the number of discharge operations read out from said memory means and the number of discharge operations as an electrode life.

3. An apparatus according to claim 1, wherein said probe has a built-in battery; and said life detecting means comprises means for discharging said battery at a predetermined current for each discharge operation, means for measuring a voltage of said battery, and display means for displaying a measurement of said measuring means in correspondence with the number of discharge operations.

4. An apparatus according to claim 1, wherein said life detecting means comprises an electrolytic integrating meter arranged in said probe, and means for supplying a current to said electrolytic integrating meter for each discharge operation.

5. An apparatus according to claim 1, wherein said life detecting means comprises current detecting means, coupled to said probe re-use inhibiting means, for detecting a current flow in said discharge electrodes for each discharge operation, means for counting the current detection by said current detecting means, and comparing means for comparing the count of said counting means with the life.

6. An apparatus according to claim 5, wherein said probe re-use inhibiting means is turned off by an output from said comparing means, and comprises a switching element for cutting off said power supply means.

7. An apparatus according to claim 1, wherein said power supply means comprises means for generating a trigger signal for applying a discharge voltage to said discharge electrodes, and said life detecting means comprises a pulse motor which is rotated in response to the trigger signal and rotational amount detecting means for detecting a predetermined rotational amount of said pulse motor.

8. An apparatus according to claim 7, wherein said rotational amount detecting means comprises a rotary plate coupled to said pulse motor, a conductor arranged in an arcuated form in said rotary plate and having a length corresponding to a predetermined rotational amount of said motor, and a contact conductor in contact with said conductor.

9. An apparatus according to claim 1, wherein said power supply means comprises means for generating a trigger signal for applying a discharge voltage to said discharge electrodes; and said life detecting means comprises an electromagnetic plunger actuated in response to the trigger signal, a ratchet mechanism actuated by said electromagnetic plunger, a movable member moved by said ratchet mechanism, and means for detecting the life from an amount of motion of said movable member.

10. An apparatus according to claim 1, wherein said power supply means comprises means for generating a trigger signal for applying a discharge voltage to said discharge electrodes; and said life detecting means comprises a laser for generating a laser beam in response to the trigger signal, a resistor member having a resistor film burnt by the laser beam, and means for measuring a resistance of said resistor member and for detecting the life from the measured resistance.

11. An apparatus according to claim 1, wherein said probe comprises a resistor unit having a plurality of resistors which are fused at different voltages; said detecting means comprises resistance detecting means for measuring a resistance of said resistor unit and means for applying to said resistor unit different voltages for sequentially disconnecting said resistors upon each predetermined number of discharge operations, said inhibit signal being generated in response to a predetermined measured value of said resistance detecting means; and said inhibiting means inhibits said power supply means to prevent use of the probe beyond said service life.

12. An apparatus according to claim 11, wherein said life detecting means includes display means for signalling an end of life in response to a predetermined detection value of said resistance detecting means.

13. An apparatus according to claim 11, wherein said detecting means includes display means for displaying a detected value of said resistance detecting means.

14. An apparatus according to claim 1, wherein said life detecting means comprises memory means, arranged in said probe, for storing the number of discharge operations.

15. An apparatus according to claim 1, wherein said life detecting means comprises switching means having a plurality of switching stages switched upon each use of said probe and corresponding at least to the electrode life.

16. An apparatus according to claim 15, wherein said probe has a connector, and said switching means has a fuse member with a plurality of fuses which are arranged in said connector of said probe in a switchable manner and are blown one by one upon each use of said probe.

17. An apparatus according to claim 15, wherein said probe has a connector, and said switching means has a plurality of connectors which are in series coupled to said connector of said probe and which are removed one by one upon each use of said probe.

18. An apparatus according to claim 15, wherein said probe has a connector, and said switching means has a counter unit with a counter drum which is rotatably mounted on said connector of said probe and which is rotated upon each use of said probe.

19. An apparatus according to claim 1, wherein said life detecting means comprises means which changes in physical state in accordance with the number of discharge operations and actuates said re-use inhibiting means when the electrode life ends.

20. An apparatus according to claim 19, wherein said life detecting means comprises a heat-generating member for generating heat upon each discharge operation and a thermal deformation member which thermally deforms upon each discharge operation, and said re-use inhibiting means comprises a switch member for cutting off said power supply means in accordance with a predetermined deformation of said thermal deformation member.

21. An apparatus according to claim 19, wherein said life detecting means comprises a conductor member arranged in said probe and having a predetermined fatigue coefficient, and means for providing a bending force to said conductor member and for functioning said re-use inhibiting means by fracturing said conductor member by fatigue thereof.

22. An apparatus according to claim 1, wherein said life detecting means comprises means for detecting a gap between said discharge electrodes 23. An apparatus according to claim 22, wherein said gap detecting means comprises a discharge tube for discharging in response to the predetermined voltage applied to said discharge electrodes.

24. An apparatus according to claim 1, wherein said life detecting means comprises means for alarming at the end of electrode life.

25. A stone disintegrator apparatus comprising:
a probe having discharge electrodes;
power supply means for applying a discharge voltage to said probe in order to allow said discharge electrodes to discharge;
means for measuring at least one of the number of discharges and the number of operations of said probe from its installation to output a measuring signal;
detection means including means for electrically blowing at least one member in response to the measuring signal;
means for establishing a service life of said probe by the at least one member blown to output a service life signal; and
means responsive to the establishing means for executing at least one of a plurality of operations including inhibiting use of said probe and indicating that the use of said probe has been inhibited.

26. An apparatus according to claim 25, wherein said detection means comprises a resistor unit provided on said probe and having a plurality of resistors which are fused at different voltages; said means for establishing a service life comprises resistance detecting means for measuring a resistance of said resistor unit and means for applying to said resistor unit different voltages for sequentially disconnecting said resistors upon each predetermined number of discharge operations, said service life signal being generated in response to a predetermined measured value of said resistance detecting means; and said executing means inhibits said power supply means to prevent use of the probe beyond said service life.

27. An apparatus according to claim 26, wherein said means for establishing a service life includes display means for displaying a detected value of said resistance detecting means.

* * * * *